United States Patent [19]

Emmrich et al.

[11] Patent Number: 5,796,489

[45] Date of Patent: Aug. 18, 1998

[54] HOLLOW VACUUM-TIGHT CERAMIC SHAPED BODY

[76] Inventors: Roland Emmrich, Gillestrasse 8, 07743 Jena; Gerhardt Krippl, August-Bebel-Strasse 19, D-07646 Stadtroda, both of Germany

[21] Appl. No.: 635,885

[22] PCT Filed: Oct. 20, 1993

[86] PCT No.: PCT/DE93/01000

§ 371 Date: Jul. 29, 1996

§ 102(e) Date: Jul. 29, 1996

[87] PCT Pub. No.: WO95/11444

PCT Pub. Date: Apr. 27, 1995

[51] Int. Cl.⁶ ............................................. G01N 21/00
[52] U.S. Cl. ............................................. 356/440
[58] Field of Search ............................ 356/440, 436–439

[56] References Cited

U.S. PATENT DOCUMENTS 5,044,755  9/1991  Landa et al. ........................ 356/440
5,046,854  9/1991  Weller et al. ........................ 356/440

FOREIGN PATENT DOCUMENTS 3509532  8/1986  Germany.
293 338  8/1991  Germany.

Primary Examiner—David C. Nelms
Assistant Examiner—Amanda Merlino
Attorney, Agent, or Firm—Cesari and McKenna, LLP

[57] ABSTRACT

A hollow vacuum-tight shaped body made of ceramic material for measuring transmission and absorption of electromagnetic radiation in liquids and gases is characterized by the fact that the ceramic material consists principally of $Al_2O_3$ and has one or a plurality of apertures of any size, which are permanently and integrally closed by a material which is permeable to electromagnetic radiation in the wavelength range from 180 nm to 5.5 μm.

4 Claims, 2 Drawing Sheets

Fig. 1A
Fig. 1B
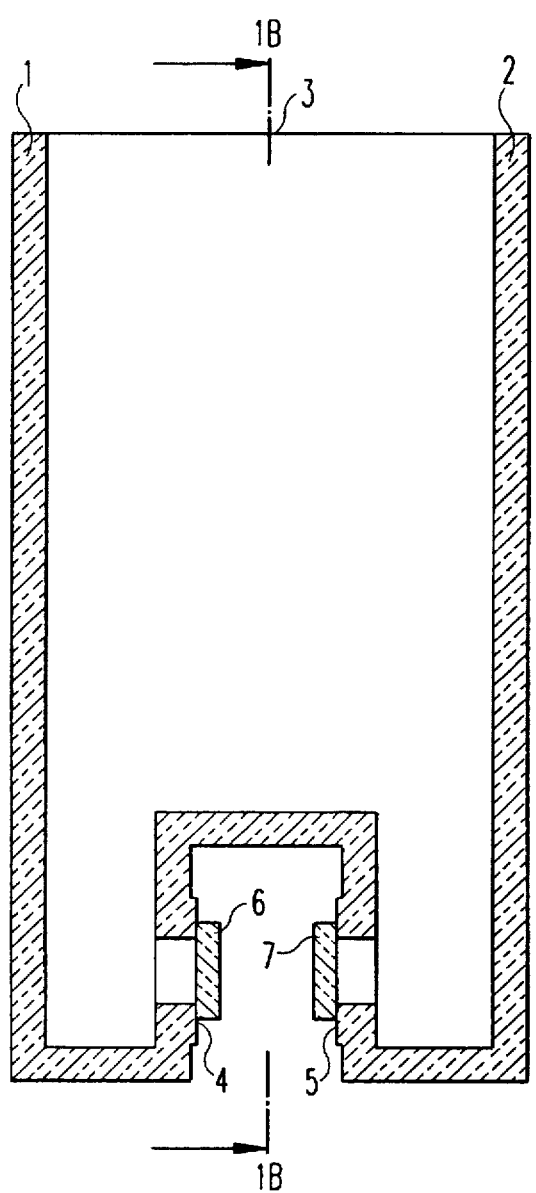
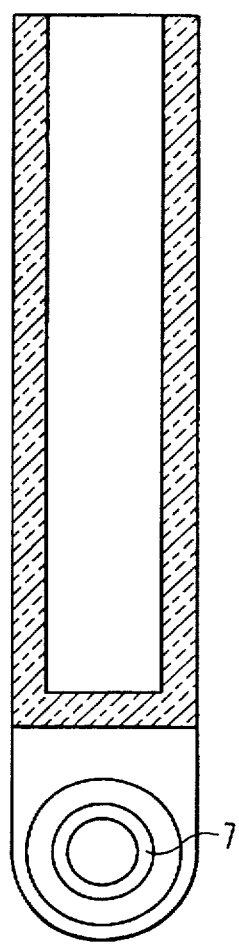

Fig. 2
Fig. 3
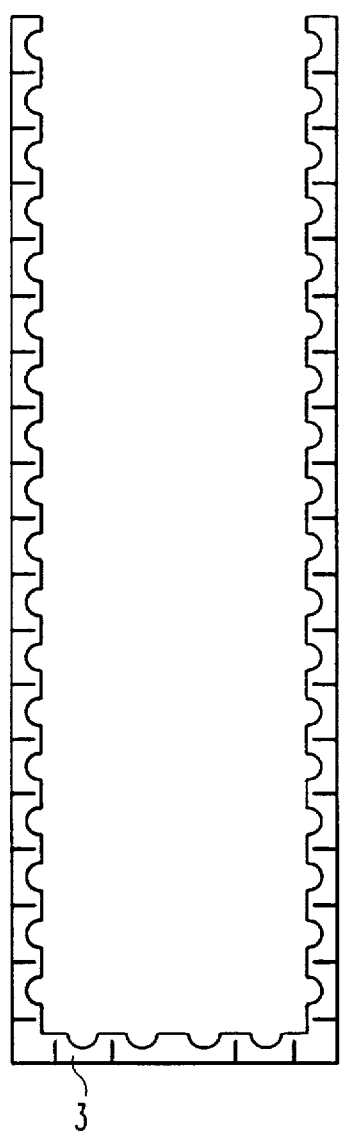
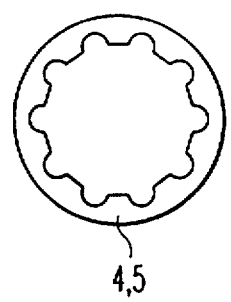

HOLLOW VACUUM-TIGHT CERAMIC SHAPED BODY

The invention relates to a hollow vacuum-tight shaped body made of ceramic material for measuring transmission and absorption of electromagnetic radiation in liquids and gases, for completing spectrometers for transmission and absorption measurement under highly aggressive conditions; it may be used in a plurality of variants in optical measurement technology (spectrometry) as an optical waveguide adapter assembly.

BACKGROUND OF THE INVENTION

There are required, for measurement analysis technology, sensors with optical measuring principles which enable investigation of liquid and gaseous media even under chemically aggressive conditions and if necessary at high temperatures. On the basis of light-optical measuring principles, spectra for transmission and absorption are absorbed by means of light of variable wavelength. More recent apparatus operates on the basis of optical waveguides.

Both submerging cells (fork-) and continuous-flow (tubular) cells made of glass are used as measuring probes. In order to carry out spectroscopy even at wavelengths in the range of 200–300 nm, submerging cells of quartz glass are used. The round or oval fork arms, in which the optical system is protected from the medium being investigated, are produced by glass-blowing. The disadvantage is the inaccuracy of the medium coating thickness due to the manufacturing process.

More accurate structures of quartz glass are manufactured as prismatic fork arrangements by soldering or wringing/diffusion welding (Company title: Carl Zeiss Oberkochen, Submerging probe TS 5). This construction is considerably more accurate. It has however the drawback that the joining zones, with glass solder, are not very chemically resistant. In the case of diffusion-welded cells, the chemical resistance of quartz glass is essential for the range of possible operational conditions; this however is less than that of ceramics. No other glass material is known for the short-wave spectroscopy range.

SUMMARY OF THE INVENTION

The object of the invention is to provide a hollow vacuum-tight ceramic shaped body which may be of complex geometric structure, and which has openings which are closed in a thermally and chemically resistant manner by material which is permeable to electromagnetic radiation, with a highly precise medium coating thickness of the closure medium.

This object is achieved according to the invention by a hollow vacuum-tight shaped body made of ceramic material for measuring transmission and absorption of electromagnetic radiation in liquids and gases, in that the ceramic material consists principally of $Al_2O_3$ ceramics, and has one or a plurality of apertures of any size which are integrally and permanently closed by optical windows of material which is permeable to electromagnetic radiation in the wavelength range from 180 nm to 5.5 μm. Before the sintering process, a green sintering ceramic film is arranged between the aperture and the material which is permeable to electromagnetic radiation in the wavelength range from 180 nm to 5.5 μm, the joining being brought about by a sintering process at a surface pressure of from 0.2 to 4 MPa such that it is integral, permanent and vacuum-tight. If the shaped body has a complex structure, it can comprise at least two ceramic shaped body parts, a green sintering ceramic film, structured according to the shape of the surfaces to be connected, likewise being disposed therebetween. Further embodiment of the invention may be seen in the sub-claims.

The advantage of the invention resides in the fact that the hollow vacuum-tight shaped body consists principally of $Al_2O_3$ ceramics, its apertures being closed by optical windows of a material which is permeable to electromagnetic radiation of from 180 nm to 5.5 μm, particularly sapphire, and whose medium coating thickness is of high precision, with excellent chemical and thermal resistance, and in that, for example when the shaped body is of complex structure, it may be assembled from a plurality of shaped body parts by means of the application of a special joining technique. In cases where only specific electromagnetic radiation should pass through the apertures, and the question of aggressiveness of the medium under investigation is of no significance, another material, for example one which admits only visible electromagnetic radiation, can also be used.

BRIEF DESCRIPTION OF THE DRAWINGS

The invention will be explained in more detail in the following with reference to an embodiment given by way of example. The following are shown in the associated drawings, in which:

FIG. 1A is a longitudinal sectional view of a hollow vacuum-tight shaped body according to the invention;

FIG. 1B is a sectional view taken along line 1B—1B of FIG. 1A;

FIG. 2: is cross-section through a green sintering film for joining two shaped body parts and FIG. 3: is cross-section through a green sintering film for joining shaped body and optical window.

DESCRIPTION OF THE PREFERRED EMBODIMENTS

FIGS. 1A and 1B show a hollow vacuum-tight shaped body made of ceramic material. $Al_2O_3$ ceramics has been discovered to be a suitable material for the shaped body. The shaped body comprises two ceramic shaped body parts (1 and 2), between which is located a green sintering ceramic film (3). Green sintering films are unsintered, i.e. sinterable ceramic films. The shaped body or the ceramic shaped body parts (1 and 2) have apertures of any size, which are integrally and permanently closed by windows for investigating liquid or gaseous media. In order to investigate these media, electromagnetic radiation can be necessary in the region outside the range of visible light. Sapphire is known as a material which is permeable to electromagnetic radiation from 180 nm to 5.5. μm, and whose medium coating thickness is highly precise. Sapphire is suitable for the most demanding optical, thermal and chemical requirements; it is chemically and thermally more resistant that quartz glass and is an excellent material optically. Therefore the apertures in the ceramic shaped body parts (1 and 2) were closed by two sapphire windows (6 and 7), this being rendered possible by the technique to be described later. Located between the ceramic shaped body part (1) and the sapphire window (6) there was disposed a green sintering ceramic film (4), and between the ceramic shaped body part (2) and the sapphire window (7) a green sintering ceramic film (5). It has proved advantageous to structure the film parts for joining ceramic shaped bodies or ceramic shaped body parts together and with sapphire windows in accordance with the surfaces to be joined. Under sufficient thermal action, ceramic films shrink in the x–y and z directions. With green sintering ceramic films used for joining, the shrinkage in the x–y direction (perpendicular to the direction of the application of force) is suppressed. Shrinkage only occurs in the z direction, the volume shrinkage corresponding approximately to that of freely sintering film. Suppression of the shrinkage in the x–y direction can only be effected by a rearrangement of the ceramic particles in the film under the effect of the force during joining. Due to this, tensions can arise in the x–y direction. If the ceramic films contain large quantities of glass-forming oxides as an auxiliary sintering means, a large proportion of the possible tensions are reduced by the fact that the glass phases occurring facilitate rearrangement of the ceramic particles due to their viscosity at joining temperature. Excessive residual tensions are evidenced by shell-shaped welling-out of the sapphire in the region of the join zone. The residual tensions present are greater in proportion as they can accumulate over an existing distance in the x–y direction. A means of reducing the residual tensions is found in limiting the free distance in the x–y direction by structuring the green sintering films (3, 4, 5). A structured foil section, e.g. a unshaped film (3), for joining together ceramic shaped body parts (1; 2) is shown in FIG. 2. An alternating arrangement of straight-line incisions is effected, extending from one edge of the film to beyond the center, and of semicircular incisions, extending from the other edge of the film as far as the center. FIG. 3 shows another structured circular film (4; 5) for joining the shaped body to optical windows, e.g. sapphire windows (6; 7). In this case semicircular incisions extend on the internal diameter, extending from the edge of the film as far as the center, at regular intervals.

In cases where only specific electromagnetic rays are to pass through the optical windows, and the question of aggressiveness of the medium under investigation is of no significance, another material, for example one which admits only visible electromagnetic radiation, can also be used.

By subdividing into constructive units which are convenient in manufacturing terms, the most varied constructions can be produced by means of these films (3; 4; 5) and special devices. Any "seal-like" intermediate structures may be manufactured from the green sintering films by means of cutting tools or lasers. The "seal-like" structured films, produced in the required shape, are applied respectively to each of the surfaces to be joined. In order to construct probes which are highly resistant chemically and thermally, and whose determined coating thickness volume meets extremely close tolerances, a special technique is required. The parts to be joined are held in position by simple devices.

After installation in a press-like device, the parts to be joined are integrally joined (welded) at temperatures of 950°–1500° C., at surface pressures of 0.2–4 MPa and with a retention time of the temperature of 5–90 minutes. When circular foil sections are used, sapphire windows can be joined to any other shaped bodies. If for constructive or technical reasons the shaped bodies comprise a plurality of constructive members, (in this case the various variants of cell body), these may be welded in the same way. Advantageous constructions are possible when all the components for the cell can be welded in one cycle. Sequences of welding processes are however also possible.

Depending on the variant of the cell involved, the coupling and decoupling optical systems For the optical waveguide system are located behind the sapphire windows. For example, FIG. 1A shows optical elements 8 in body 1 for deflecting a beam 9 so that the beam can pass into the body, through the windows 8 and out again. In the case of the fork-shaped cell body, the optical path of the beam is still rotated through 90°. In the case of the tubular continuous-flow cell, the coupling and decoupling optical systems are flush in configuration. In principle, the fork-shaped cell can also be provided with a "collar-like" flange for lateral insertion in pipelines. Hollow shaped bodies with sapphire windows, joined according to the method described, are vacuum-tight and thus gas- and liquid-tight.

Corresponding optical systems can be disposed therein. This eliminates the time- and cost-intensive, often dangerous removal of the sample and its placing into a cell, which is then inserted into the spectrometer.

We claim:

1. A hollow vacuum-tight shaped body made of ceramic material for measuring transmission and absorption of electromagnetic radiation in liquids and gases, wherein the ceramic material mainly consists of $Al_2O_3$ ceramic having at least one aperture each with a sapphire window permeable to electromagnetic radiation of a wavelength range from 180 nm to 5.5 μm, and wherein for the sealing between the sapphire window and the aperture wall a green ceramic film corresponding to the surfaces to be joined is arranged, forming an integral, permanent, vacuum-tight seal by a sintering process with a surface pressure of 0.2 to 4 MPa.

2. The hollow vacuum-tight shaped body according to claim 1, wherein the at least one aperture is positioned such that the electromagnetic radiation can enter and exit the shaped body through the optical windows.

3. The hollow vacuum-tight shaped body according to claim 1, wherein optical components for deviating the optical beam path are disposed in the interior of the shaped body such that the electromagnetic radiation can enter and exit the shaped body through the optical windows.

4. The hollow vacuum-tight shaped body according to claim 1, wherein the green sintering ceramic films are structured to the shape of the surfaces to be joined and to a minimization of the maximum free distance in the x–y direction.

* * * * *